(12) United States Patent
Garcia Castro et al.

(10) Patent No.: US 8,790,424 B2
(45) Date of Patent: Jul. 29, 2014

(54) COPOLYMER AND USE THEREOF FOR IMPROVING THE COLD FLOW PROPERTIES OF MIDDLE DISTILLATE FUELS

(75) Inventors: Ivette Garcia Castro, Ludwigshafen (DE); Uwe Rebholz, Mehlingen (DE); Irene Troetsch-Schaller, Bissersheim (DE); Markus Brym, Limburgerhof (DE); Jan Strittmatter, Mannheim (DE); Michael Schroers, Bad Duerkheim (DE)

(73) Assignee: BASF SE, Ludwigshafer (DE)

( * ) Notice: Subject to any disclaimer, the term of this patent is extended or adjusted under 35 U.S.C. 154(b) by 86 days.

(21) Appl. No.: 13/432,554

(22) Filed: Mar. 28, 2012

(65) Prior Publication Data
US 2012/0247001 A1 Oct. 4, 2012

Related U.S. Application Data

(60) Provisional application No. 61/469,101, filed on Mar. 30, 2011.

(51) Int. Cl.
*C10L 1/196* (2006.01)
*C07D 407/14* (2006.01)

(52) U.S. Cl.
USPC ............................................. 44/351; 549/252

(58) Field of Classification Search
USPC ............................................. 44/351; 549/252
See application file for complete search history.

(56) References Cited

U.S. PATENT DOCUMENTS

| | | | | |
|---|---|---|---|---|
| 3,447,915 | A * | 6/1969 | Otto ................................ | 44/393 |
| 6,458,174 | B1 | 10/2002 | Krull et al. | |
| 2005/0126071 | A1 | 6/2005 | Krull et al. | |
| 2007/0094920 | A1* | 5/2007 | Ahlers et al. ................... | 44/393 |
| 2010/0251604 | A1 | 10/2010 | Maehling et al. | |
| 2011/0258917 | A1 | 10/2011 | Garcia Castro et al. | |
| 2011/0271586 | A1 | 11/2011 | Maehling et al. | |
| 2012/0005951 | A1 | 1/2012 | Maehling et al. | |

FOREIGN PATENT DOCUMENTS

| | | |
|---|---|---|
| DE | 199 01 803 A1 | 7/2000 |
| EP | 1 541 664 A1 | 6/2005 |
| EP | 1 746 147 A1 | 1/2007 |
| WO | WO 2008/113757 A1 | 9/2008 |

OTHER PUBLICATIONS

U.S. Appl. No. 13/781,929, filed Mar. 1, 2013, Strittmatter, et al.
International Search Report and Written Opinion issued Jun. 12, 2012, in PCT/EP2012/055383, filed Mar. 27, 2012 with English translation of category of cited documents.
U.S. Appl. No. 13/712,297, filed Dec. 12, 2012 Hansch, et al.
U.S. Appl. No. 13/783,708, filed Mar. 4, 2013, Strittmatter, et al.

* cited by examiner

*Primary Examiner* — Prem C Singh
*Assistant Examiner* — Chantel Graham
(74) *Attorney, Agent, or Firm* — Oblon, Spivak, McClelland, Maier & Neustadt, L.L.P.

(57) ABSTRACT

A copolymer obtainable by free-radical copolymerization of
(i) monomer units of the structure M1

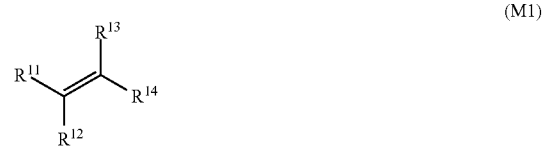

in which the variables are each hydrogen, alkyl groups, carboxyl groups or carboxyl derivative moieties, and
(ii) monomer units of the structure M2

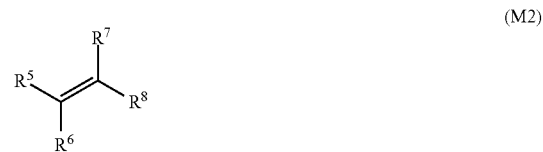

in which $R^5$ is the radical of a carboxylic ester of the formula $-A-CO-O-R^{10}$ where A is an alkylene group and $R^{10}$ is a hydrocarbyl radical, and in which $R^6$, $R^7$ and $R^8$ are each hydrogen or alkyl radicals,
and subsequent polymer-analogous reaction of the product formed with a long-chain hydrocarbyl alcohol.

This copolymer is suitable for improving the cold flow properties of middle distillate fuels, especially those which consist of or comprise biofuel oils.

11 Claims, No Drawings

COPOLYMER AND USE THEREOF FOR IMPROVING THE COLD FLOW PROPERTIES OF MIDDLE DISTILLATE FUELS

The present invention relates to a novel copolymer based on (i) ethylenically α,β-unsaturated dicarboxylic acids or derivatives thereof and (ii) ethylenically unsaturated carboxylic esters in which the ethylenic double bond is not conjugated to the carboxyl carbon atom, some or all of the carboxyl groups originating from the ethylenically α,β-unsaturated dicarboxylic acids having been esterified with a long-chain alcohol.

The present invention further relates to a process for preparing this copolymer by free-radical copolymerization.

The present invention further relates to the use of this copolymer for improving the cold flow properties of middle distillate fuels, especially for lowering the CP value thereof, and to middle distillate fuels with a content of this copolymer itself.

Middle distillate fuels of fossil origin, especially gas oils, diesel oils or light heating oils, which are obtained from mineral oil, have different contents of paraffins depending on the origin of the crude oil. At low temperatures, there is precipitation of solid paraffins at the cloud point ("CP"). In the course of further cooling, the platelet-shaped n-paraffin crystals form a kind of "house of cards structure" and the middle distillate fuel ceases to flow even though its predominant portion is still liquid. The precipitated n-paraffins in the temperature range between cloud point and pour point ("PP") considerably impair the flowability of the middle distillate fuels; the paraffins block filters and cause irregular or completely interrupted fuel supply to the combustion units. Similar disruptions occur in the case of light heating oils.

It has long been known that suitable additives can modify the crystal growth of the n-paraffins in middle distillate fuels. Very effective additives prevent middle distillate fuels from solidifying even at temperatures a few degrees Celsius below the temperature at which the first paraffin crystals crystallize out. Instead, fine, readily crystallizing, separate paraffin crystals are formed, which, even when the temperature is lowered further, pass through filters in motor vehicles and heating systems, or at least form a filtercake which is permeable to the liquid portion of the middle distillates, so that disruption-free operation is ensured. The effectiveness of the flow improvers is typically expressed, in accordance with European standard EN 116, indirectly by measuring the cold filter plugging point ("CFPP"). Cold flow improvers or middle distillate flow improvers ("MDFIs") of this kind which are used have for a long time included, for example, ethylene-vinyl carboxylate copolymers such as ethylene-vinyl acetate copolymers ("EVA").

One disadvantage of these additives is that the paraffin crystals modified in this way, owing to their higher density compared to the liquid portion, tend to settle out more and more at the bottom of the vessel in the course of storage of the middle distillate fuel. As a result, a homogeneous low-paraffin phase forms in the upper part of the vessel, and a biphasic paraffin-rich layer at the bottom. Since the fuel is usually drawn off just above the vessel bottom both in vehicle fuel tanks and storage or supply tanks of mineral oil dealers, there is the risk that the high concentration of solid paraffins leads to blockages of filters and metering devices. The further the storage temperature is below the precipitation temperature of the paraffins, the greater this risk becomes, since the amount of paraffin precipitated increases with falling temperature. In particular, fractions of biodiesel also enhance this undesired tendency of the middle distillate fuel to paraffin sedimentation. By virtue of the additional use of paraffin dispersants or wax antisettling additives ("WASAs"), the problems outlined can be reduced.

In view of declining world mineral oil reserves and the discussion surrounding the environmentally damaging consequences of the consumption of fossil and mineral fuels, interest is rising in alternative energy sources based on renewable raw materials. These include in particular native oils and fats of vegetable or animal origin. These are in particular triglycerides of fatty acids having from 10 to 24 carbon atoms, which are converted to lower alkyl esters such as methyl esters. These esters are generally also referred to as "FAMEs" (fatty acid methyl esters).

As is the case for middle distillates of fossil origin, crystals which can likewise block motor vehicle filters and metering devices precipitate out in the course of cooling of such FAMEs. However, these crystals do not consist of n-paraffins but rather of fatty acid esters; in spite of this, it is possible to characterize fuels based on FAMEs with the same parameters as for the middle distillates of fossil origin (CP, PP, CFPP).

The FAMEs mentioned and mixtures of these FAMEs with middle distillates generally have poorer cold performance than middle distillates of fossil origin alone. In the case of mixtures with middle distillates of fossil origin, the addition of the FAMEs increases the tendency to form paraffin sediments. In particular, however, the FAMEs mentioned, when they are intended to replace middle distillates of fossil origin partly or completely as biofuel oils, have excessively high CFPP values and in particular excessively high PP values, such that they cannot be used without difficulty as a fuel or heating oil according to the current country- and region-specific requirements. The increase in the viscosity in the course of cooling also influences the cold properties in FAMEs to a greater extent than in middle distillates of fossil origin.

There have already been proposals of additives which are intended to improve the cold properties, for example the CP value, of middle distillate fuels. For instance, EP 1 746 147 A1 describes copolymers of mono-$C_8$- to —$C_{30}$-alkyl maleates, maleic anhydride and $C_8$- to $C_{30}$-alkenes for this use in heating oils and diesel fuels, which may also comprise biofuel oils in amounts up to 30% by weight.

It was an object of the present invention to provide products which bring about improved cold performance in middle distillate fuels, especially in those based on biofuel oils ("biodiesel"), which are based on fatty acid esters (FAMEs). More particularly, the pour point (PP value) for such fuels should be effectively lowered.

The object is achieved in accordance with the invention by a copolymer which is formed from
(i) 10 to 90 mol % of repeat units of the structure W1

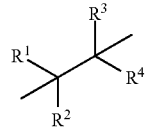
(W1)

in which the variables $R^1$ and $R^2$ are each hydrogen, $C_1$- to $C_4$-alkyl or carboxyl ester moieties of the formula —$COOR^9$ where $R^9$ is a $C_6$- to $C_{30}$-hydrocarbyl radical and where one of the variables $R^1$ and $R^2$ is hydrogen or $C_1$- to $C_4$-alkyl and the other is a carboxyl ester moiety of the formula —$COOR^9$, and in which variables $R^3$ and $R^4$ are each hydrogen, $C_1$- to $C_4$-alkyl, carboxyl ester moieties of the formula —$COOR^9$ where $R^9$ is a $C_6$- to $C_{30}$-hydrocarbyl radical, or carboxyl groups which may also be present in the form of the alkali metal, alkaline earth metal or ammonium salts thereof, where one of the variables $R^3$ and $R^4$ is hydrogen or $C_1$- to $C_4$-alkyl and the other is a carboxyl ester moiety of the formula —$COOR^9$ and/or a carboxyl group which may also be present in the form of the alkali metal, alkaline earth metal or ammonium salt thereof, and (ii) 90 to 10 mol % of repeat units of the structure W2

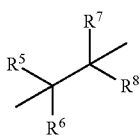

in which the variable $R^5$ is the radical of a carboxylic ester of the formula

-A-CO—O—$R^{10}$ where the variable A is a $C_1$- to $C_{20}$-alkylene group and the variable $R^{10}$ is a $C_1$- to $C_{30}$-hydrocarbyl radical, and in which the variables $R^6$, $R^7$ and $R^8$ are each independently hydrogen or $C_1$- to $C_8$-alkyl, where the sum of the repeat units W1 and W2 adds up to 100 mol %.

In the context of the present invention, the following definitions apply to generically defined radicals:

Hydrocarbyl radicals are radicals composed of linear or branched hydrocarbon chains, which may also comprise, to a minor extent, heteroatoms such as oxygen, nitrogen or halogen atoms, for example chlorine, and/or aprotic functional groups, for example carboxyl ester groups, cyano groups or nitro groups, without significantly influencing the predominantly hydrophobic hydrocarbon character of these radicals, and generally do not have any carbon-carbon double or triple bonds and also no other unsaturations which could disrupt formation of copolymers from (i) and (ii). Preferred $C_1$- to $C_{30}$-hydrocarbyl radicals are, however, pure cycloalkyl radicals which may also bear alkyl side chains, and/or especially pure linear or branched alkyl radicals with the corresponding same total number of carbon atoms in each case.

Examples of such $C_1$- to $C_4$- or $C_1$- to $C_8$- or $C_1$- to $C_{30}$- or $C_6$- to $C_{30}$- or $C_8$- to $C_{16}$- or $C_{10}$- to $C_{14}$-alkyl- or -cycloalkyl radicals are methyl, ethyl, n-propyl, isopropyl, n-butyl, 2-butyl, isobutyl, tert.-butyl, pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, n-nonyl, isononyl, n-decyl, 2-propylheptyl, n-undecyl, n-dodecyl, n-tridecyl, isotridecyl, n-tetradecyl, n-hexadecyl, n-octadecyl and n-eicosyl, and, as corresponding cycloalkyl radicals which may also bear alkyl side chains, cyclopentyl, 2- or 3-methylcyclopentyl, 2,3-, 2,4- or 2,5-dimethylcyclopentyl, cyclohexyl, 2-, 3- or 4-methylcyclohexyl, 2,3-, 2,4-, 2,5-, 2,6-, 3,4-, 3,5- or 3,6-dimethylcyclohexyl, cycloheptyl, 2-, 3- or 4-methylcycloheptyl, cyclooctyl, 2-, 3-, 4- or 5-methylcyclooctyl.

Stable cycloalkyl radicals which are useful here typically bear at least 4 carbon atoms in the ring.

Suitable $C_1$- to $C_{20}$- or linear $C_4$- to $C_{12}$-alkylene groups for the variable A are in principle all divalent linear or branched saturated aliphatic hydrocarbon structures, but preference is given to polyalkylene groups of the formula $(CH_2)_m$— in which m is from 1 to 20, especially 2 to 16, in particular 4 to 12, most preferably 6 to 10, for example 7, 8 or 9. In the case of branched alkylene groups, in addition to the am-bonding hydrocarbon structures, also suitable are nonlinear bridging members such as 1,1-ethylene, 1,1-propylene, 2,2-propylene, 1,2-propylene, 2-methyl-1,4-butylene, 3-methyl-1,5-pentylene or 2-ethyl-1,6-hexylene.

The inventive copolymer may in principle have a random, block or alternating structure. An alternating structure is preferred. Accordingly, the inventive copolymer is preferably formed from 25 to 75 mol %, especially 45 to 55 mol %, in particular 49 to 51 mol %, of repeat units of the structure W1, and 75 to 25 mol %, especially 55 to 45 mol %, in particular 51 to 49 mol %, of repeat units of the structure W2.

In a preferred embodiment, the variables in the repeat unit W1 are each defined as follows:

$R^1$ is hydrogen, $R^2$ is a carboxyl ester moiety of the formula —$COOR^9$ where $R^9$ is a $C_8$- to $C_{16}$-hydrocarbyl radical, $R^3$ is hydrogen, $R^4$ is a carboxyl ester moiety of the formula —$COOR^9$ where $R^9$ is a $C_8$- to $C_{16}$-hydrocarbyl radical, especially a $C_{10}$-$C_{14}$-hydrocarbyl radical, and/or a carboxyl group which may also be present in the form of the alkali metal, alkaline earth metal or ammonium salt thereof.

In a further preferred embodiment, the variables in the repeat unit W2 are each defined as follows:

$R^5$ is the radical of a carboxylic ester of the formula -A-CO—O—$R^{10}$ where A is a linear $C_4$- to $C_{12}$-alkylene group and $R^{10}$ is a $C_1$- to $C_4$-alkyl radical, $R^6$, $R^7$ and $R^8$ are each hydrogen.

If carboxyl groups in the repeat unit W1 should be present in the form of the alkali metal, alkaline earth metal or ammonium salts thereof, what is meant here is, for example, the lithium, sodium, potassium, magnesium or calcium salts. In the case of ammonium salts, the ammonium cation may bear on the nitrogen, for example, up to 4 identical or different alkyl substituents such as methyl, ethyl, n-propyl or n-butyl.

The inventive copolymer can advantageously be prepared by known and customary free-radical polymerization techniques. The present invention therefore also provides a copolymer which is obtainable by free-radical copolymerization of (i) 10 to 90 mol %, preferably 25 to 75 mol %, especially 45 to 55 mol %, in particular 49 to 51 mol %, of monomer units of the structure M1

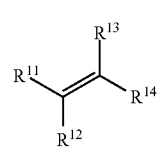

in which the variables $R^{11}$, $R^{12}$, $R^{13}$ and $R^{14}$ are each independently hydrogen, $C_1$- to $C_4$-alkyl, carboxyl groups, carboxyl ester moieties of the formula —$COOR^{15}$ where $R^{15}$ is a $C_1$- to $C_4$-alkyl radical, or carbonyl halide moieties of the formula —COX where X is fluorine, chlorine, bromine or iodine, with the proviso that M1 comprises two vicinal carboxyl groups and/or carboxyl ester moieties of this kind in cis or trans positions to one another, where vicinal carboxyl groups in cis positions may also be present in the form of the cyclic anhydride thereof, and (ii) 90 to 10 mol %, preferably 75 to 25 mol %, especially 55 to 45 mol %, in particular 51 to 49 mol %, of Monomer units of the structure M2

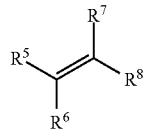

(M2)

in which the variable $R^5$ is the radical of a carboxylic ester of the formula

-A-CO—O—$R^{10}$ where the variable A is a $C_1$- to $C_{20}$-alkylene group, especially a linear $C_4$- to $C_{12}$-alkylene group, and the variable $R^{10}$ is a $C_1$- to $C_{30}$-hydrocarbyl radical, especially a $C_1$- to $C_8$-hydrocarbyl radical, in particular a to $C_4$-alkyl radical, and in which the variables $R^6$, $R^7$ and $R^8$ are each independently hydrogen or $C_1$- to $C_8$-alkyl, where the sum of the monomer units M1 and M2 adds up to 100 mol %, and subsequent polymer-analogous reaction of the product formed with at least 1 to 2 mol of a $C_6$- to $C_{30}$-hydrocarbyl alcohol per mole of monomer M1 used.

The present invention also provides a process for preparing the inventive copolymer, which comprises free-radically copolymerizing (i) 10 to 90 mol %, preferably 25 to 75 mol %, especially 45 to 55 mol %, in particular 49 to 51 mol %, of monomer units of the structure M1

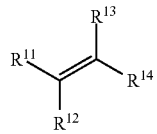

(M1)

in which the variables $R^{11}$, $R^{12}$, $R^{13}$ and $R^{14}$ are each independently hydrogen, $C_1$- to $C_4$-alkyl, carboxyl groups, carboxyl ester moieties of the formula —COOR$^{15}$ where $R^{15}$ is a $C_1$- to $C_4$-alkyl radical, or carbonyl halide moieties of the formula —COX where X is fluorine, chlorine, bromine or iodine, with the proviso that M1 comprises two vicinal carboxyl groups and/or carboxyl ester moieties of this kind in cis or trans positions to one another, where vicinal carboxyl groups in cis positions may also be present in the form of the cyclic anhydride thereof, and (ii) 90 to 10 mol %, preferably 75 to 25 mol %, especially 55 to 45 mol %, in particular 51 to 49 mol %, of monomer units of the structure M2

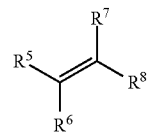

(M2)

in which the variable $R^5$ is the radical of a carboxylic ester of the formula

-A-CO—O—$R^{10}$ a linear $C_4$- to $C_{12}$-alkylene group, and the variable $R^{10}$ is a $C_1$- to $C_{30}$-hydrocarbyl radical, especially a $C_1$- to $C_5$-hydrocarbyl radical, in particular a $C_1$- to $C_4$-alkyl radical, and in which the variables $R^6$, $R^7$ and $R^8$ are each independently hydrogen or $C_1$- to $C_4$-alkyl, where the sum of the monomer units M1 and M2 adds up to 100 mol %, with one another and subsequently reacting the product formed in a polymer-analogous manner with at least 1 to 2 mol of a $C_6$- to $C_{30}$-hydrocarbyl alcohol per mole of monomer M1 used.

The monomer components (i) are ethylenically α,β-unsaturated dicarboxylic acids or derivatives thereof, such as esters, cyclic anhydrides or carbonyl halides such as carbonyl chlorides. In a preferred embodiment, in the copolymerization of M1 and M2 which is appropriately performed using free-radically decomposing initiators, maleic acid, maleic anhydride, mono- or dimethyl maleate, mono- or diethyl maleate, fumaric acid, mono- or dimethyl fumarate or mono- or diethyl fumarate are used as monomer units M1. Additionally suitable, however, as monomer units M1, are, for example, also 2-methylmaleic acid, 2-methylmaleic anhydride, 2,3-dimethylmaleic acid, 2,3-dimethylmaleic anhydride, 2-methylfumaric acid, 2,3-dimethylfumaric acid, and the mono- and dimethyl and mono- and diethyl esters of these dicarboxylic acids.

The monomer components (ii are ethylenically unsaturated carboxylic esters in which the ethylenic double bond is not conjugated to the carboxylcarbon atom. Preference is given here to using those monomer units M2 in which the variables $R^6$, $R^7$ and $R^8$ are each hydrogen, the variable $R^{10}$ is a $C_1$- to $C_4$-alkyl radical, especially methyl, ethyl, n-propyl or n-butyl, and the variable A is a linear $C_4$- to $C_{12}$-alkylene group, especially a linear $C_6$- to $C_{10}$-alkylene group, in particular a linear $C_7$-, $C_8$- or $C_s$-alkylene group.

Examples of Monomer Units M2 are:
methyl, ethyl, n-propyl and n-butyl but-3-enoate,
methyl, ethyl, n-propyl and n-butyl pent-3-enoate,
methyl, ethyl, n-propyl and n-butyl pent-4-enoate,
methyl, ethyl, n-propyl and n-butyl hex-3-enoate,
methyl, ethyl, n-propyl and n-butyl hex-4-enoate,
methyl, ethyl, n-propyl and n-butyl hex-5-enoate,
methyl, ethyl, n-propyl and n-butyl hept-3-enoate,
methyl, ethyl, n-propyl and n-butyl hept-4-enoate,
methyl, ethyl, n-propyl and n-butyl hept-5-enoate,
methyl, ethyl, n-propyl and n-butyl hept-6-enoate,
methyl, ethyl, n-propyl and n-butyl oct-3-enoate
methyl, ethyl, n-propyl and n-butyl oct-4-enoate
methyl, ethyl, n-propyl and n-butyl oct-5-enoate
methyl, ethyl, n-propyl and n-butyl oct-6-enoate
methyl, ethyl, n-propyl and n-butyl oct-7-enoate
methyl, ethyl, n-propyl and n-butyl non-3-enoate
methyl, ethyl, n-propyl and n-butyl non-4-enoate
methyl, ethyl, n-propyl and n-butyl non-5-enoate
methyl, ethyl, n-propyl and n-butyl non-6-enoate methyl, ethyl, n-propyl and n-butyl non-7-enoate
methyl, ethyl, n-propyl and n-butyl non-8-enoate
methyl, ethyl, n-propyl and n-butyl dec-3-enoate
methyl, ethyl, n-propyl and n-butyl dec-4-enoate
methyl, ethyl, n-propyl and n-butyl dec-5-enoate
methyl, ethyl, n-propyl and n-butyl dec-6-enoate
methyl, ethyl, n-propyl and n-butyl dec-7-enoate
methyl, ethyl, n-propyl and n-butyl dec-8-enoate
methyl, ethyl, n-propyl and n-butyl dec-9-enoate
methyl, ethyl, n-propyl and n-butyl undec-3-enoate
methyl, ethyl, n-propyl and n-butyl undec-4-enoate
methyl, ethyl, n-propyl and n-butyl undec-5-enoate
methyl, ethyl, n-propyl and n-butyl undec-6-enoate
methyl, ethyl, n-propyl and n-butyl undec-7-enoate
methyl, ethyl, n-propyl and n-butyl undec-8-enoate
methyl, ethyl, n-propyl and n-butyl undec-9-enoate
methyl, ethyl, n-propyl and n-butyl undec-10-enoate
methyl, ethyl, n-propyl and n-butyl dodec-3-enoate
methyl, ethyl, n-propyl and n-butyl dodec-4-enoate
methyl, ethyl, n-propyl and n-butyl dodec-5-enoate
methyl, ethyl, n-propyl and n-butyl dodec-6-enoate
methyl, ethyl, n-propyl and n-butyl dodec-7-enoate
methyl, ethyl, n-propyl and n-butyl dodec-8-enoate
methyl, ethyl, n-propyl and n-butyl dodec-9-enoate
methyl, ethyl, n-propyl and n-butyl dodec-10-enoate
methyl, ethyl, n-propyl and n-butyl dodec-11-enoate
methyl, ethyl, n-propyl and n-butyl tridec-3-enoate
methyl, ethyl, n-propyl and n-butyl tridec-4-enoate
methyl, ethyl, n-propyl and n-butyl tridec-5-enoate
methyl, ethyl, n-propyl and n-butyl tridec-6-enoate
methyl, ethyl, n-propyl and n-butyl tridec-7-enoate
methyl, ethyl, n-propyl and n-butyl tridec-8-enoate
methyl, ethyl, n-propyl and n-butyl tridec-9-enoate
methyl, ethyl, n-propyl and n-butyl tridec-10-enoate
methyl, ethyl, n-propyl and n-butyl tridec-11-enoate
methyl, ethyl, n-propyl and n-butyl tridec-12-enoate
methyl, ethyl, n-propyl and n-butyl tetradec-3-enoate
methyl, ethyl, n-propyl and n-butyl tetradec-4-enoate
methyl, ethyl, n-propyl and n-butyl tetradec-5-enoate
methyl, ethyl, n-propyl and n-butyl tetradec-6-enoate
methyl, ethyl, n-propyl and n-butyl tetradec-7-enoate
methyl, ethyl, n-propyl and n-butyl tetradec-8-enoate
methyl, ethyl, n-propyl and n-butyl tetradec-9-enoate
methyl, ethyl, n-propyl and n-butyl tetradec-10-enoate
methyl, ethyl, n-propyl and n-butyl tetradec-11-enoate
methyl, ethyl, n-propyl and n-butyl tetradec-12-enoate
methyl, ethyl, n-propyl and n-butyl tetradec-13-enoate
methyl, ethyl, n-propyl and n-butyl pentadec-3-enoate
methyl, ethyl, n-propyl and n-butyl pentadec-4-enoate
methyl, ethyl, n-propyl and n-butyl pentadec-5-enoate
methyl, ethyl, n-propyl and n-butyl pentadec-6-enoate
methyl, ethyl, n-propyl and n-butyl pentadec-7-enoate
methyl, ethyl, n-propyl and n-butyl pentadec-8-enoate
methyl, ethyl, n-propyl and n-butyl pentadec-9-enoate
methyl, ethyl, n-propyl and n-butyl pentadec-10-enoate
methyl, ethyl, n-propyl and n-butyl pentadec-11-enoate
methyl, ethyl, n-propyl and n-butyl pentadec-12-enoate
methyl, ethyl, n-propyl and n-butyl pentadec-13-enoate
methyl, ethyl, n-propyl and n-butyl pentadec-14-enoate The ethylenic double bond in all the abovementioned monomer components M2 may be in cis or trans configuration.

The two monomer components (i) and (ii) can be polymerized in the first preparation stage in substance, in suspension or preferably in solution. It is possible here to use, for each monomer component (i) and (ii), a single monomer species or a mixture of several such monomer species. The polymerization reaction is performed generally at standard pressure and under a protective gas, such as nitrogen, but it is also possible to work at elevated pressures, for example in an autoclave. The polymerization temperatures are generally 50 to 250° C., especially 90 to 210° C., in particular 120 to 180° C., typically 140 to 160° C. Suitable polymerization reactors are in principle all customary continuous or batchwise apparatuses, for example stirred tanks, stirred tank cascades, tubular reactors or loop reactors.

The polymerization is typically initiated by free-radically decomposing initiators; suitable for this purpose are air or oxygen or organic peroxides and/or hydroperoxides, and organic azo compounds. Useful organic peroxides or hydroperoxides include, for example, diisopropylbenzene hydroperoxide, cumene hydroperoxide, methyl isobutyl ketone peroxide, di-tert-butyl peroxide and tert-butyl perisononate. A suitable organic azo compound is, for example, azobisisobutyronitrile ("AIBN"). It is additionally possible to use suitable regulators such as aliphatic aldehydes or ketones, or else hydrogen, in the polymerization.

If solvents or suspension media are used in the polymerization, useful substances for this purpose are the customary high-boiling inert liquids such as aromatic hydrocarbons, e.g. toluene, xylenes or appropriate technical-grade hydrocarbon mixtures such as Solvesso® or Solvent Naphtha.

Useful $C_6$- to $C_{30}$-hydrocarbyl alcohols for the polymer-analogous reaction of the polymerization product prepared as described above in the second preparation stage are those alcohols which bear the abovementioned hydrocarbyl radicals, especially alkyl or cycloalkyl radicals. Preference is given here, however, to branched or especially linear primary $C_8$- to $C_{16}$-hydrocarbyl alcohols, in particular branched or especially linear primary $C_{10}$- to $C_{14}$-hydrocarbyl alcohols. Typical examples of such hydrocarbyl alcohols are 2-ethylhexanol, n-octanol, n-nonanol, n-decanol, 2-propyl-heptanol, n-undecanol, n-dodecanol, n-tridecanol and isotridecanol. It is also possible to use technical-grade mixtures of such medium-chain aliphatic alcohols.

The reaction of the polymerization product with the $C_6$- to $C_{30}$-hydrocarbyl alcohol or with a mixture of such alcohols is effected generally by heating at standard pressure and typically under a protective gas such as nitrogen to temperatures in the range from 50 to 200° C., especially from 90 to 180° C., in particular from 120 to 170° C., typically from 140 to 160° C. It is possible here to use acids or bases as esterification catalysts. When the esterification is complete or has attained the desired degree of conversion, workup is effected as usual. When the carboxyl group to be esterified is present as an ester of lower alcohols, i.e. as a $C_1$- to $C_4$-alkyl ester, a transesterification takes place, in which the lower alcohol is displaced in the molecule by the less volatile $C_6$- to $C_{30}$-hydrocarbyl alcohol. In this case, not only the transesterification reactions on the carboxyl functions in M1 but also transesterification reactions on the carboxyl function in M2 may take place. If the carboxyl functions in M1 are present as free carboxylic acids, as anhydrides or as carbonyl halides, a transesterification on the carboxyl function in M2 is substantially avoided.

For esterification or transesterification of the polymerization product, usually a sufficient amount of $C_6$- to $C_{30}$-hydrocarbyl alcohol is used that one or both of the carboxyl functions originating from M1 are converted to long-chain esters. The amount of $C_6$- to $C_{30}$-hydrocarbyl alcohol can also be controlled such that this degree of esterification or transesterification on the carboxyl functions on the repeat unit W1 is between 1 and 2. If the carboxyl ester function on the repeat unit W2 is likewise being, or is to be, transesterified to a long-chain ester, more than 2 mol of $C_6$- to $C_{30}$-hydrocarbyl alcohol are needed per mole of M1, for example up to 3 mol per mole of M1 when M1 and M2 are copolymerized in an equimolar ratio.

The precursor of the inventive copolymer which results from the free-radical copolymerization of the monomer units M1 and M2 and is yet to be reacted with the $C_6$- to $C_{30}$-hydrocarbyl alcohol preferably has a number-average molecular weight ($M_n$) in the range from 500 to 10 000, especially from 1000 to 5000, or alternatively a weight-average molecular weight ($M_w$) from 750 to 50 000, especially from 1500 to 25 000 (all figures in g/mol, determined in each case by gel permeation chromatography).

Based on the number of repeat units of the structures W1 and W2, the inventive copolymer comprises preferably a total of 4 to 80, especially 8 to 40, of these repeat units, and in the preferred embodiment of the alternating structure of the copolymer the numbers of W1 and W2 are in each case the same or nearly the same.

The inventive copolymer serves as a novel efficient cold flow improver in middle distillate fuels. In the context of the present invention, middle distillate fuels shall be understood to mean middle distillate fuels boiling in the range from 120 to 450° C. Such middle distillate fuels are used in particular as diesel fuel, heating oil or kerosene, particular preference being given to diesel fuel and heating oil.

Middle distillate fuels (also referred to hereinafter as "middle distillates" for short) refer to fuels which are obtained by distilling crude oil as the first process step and boil within the range from 120 to 450° C. Preference is given to using low-sulfur middle distillates, i.e. those which comprise less than 350 ppm of sulfur, especially less than 200 ppm of sulfur, in particular less than 50 ppm of sulfur. In special cases, they comprise less than 10 ppm of sulfur; these middle distillates are also referred to as "sulfur-free". They are generally crude oil distillates which have been subjected to refining under hydrogenating conditions and therefore comprise only small proportions of polyaromatic and polar compounds. They are preferably those middle distillates which have 90% distillation points below 370° C., in particular below 360° C. and in special cases below 330° C.

Low-sulfur and sulfur-free middle distillates may also be obtained from relatively heavy mineral oil fractions which cannot be distilled under atmospheric pressure. Typical conversion processes for preparing middle distillates from heavy mineral oil fractions include: hydrocracking, thermal cracking, catalytic cracking, coking processes and/or visbreaking. Depending on the process, these middle distillates are obtained in low-sulfur or sulfur-free form, or are subjected to refining under hydrogenating conditions.

The middle distillates preferably have aromatics contents of below 28% by weight, especially below 20% by weight. The content of normal paraffins is between 5 and 50% by weight, preferably between 10 and 35% by weight.

In the context of the present invention, middle distillate fuels shall also be understood here to mean those fuels which can either be derived indirectly from fossil sources such as mineral oil or natural gas, or else are prepared from biomass via gasification and subsequent hydrogenation. A typical example of a middle distillate fuel which is derived indirectly from fossil sources is the GTL ("gas-to-liquid") diesel fuel obtained by means of Fischer-Tropsch synthesis. A middle distillate is prepared from biomass, for example via the BTL ("biomass-to-liquid") process, and can be used either alone or in a mixture with other middle distillates as fuel. The middle distillates also include hydrocarbons which are obtained by the hydrogenation of fats and fatty oils. They comprise predominantly n-paraffins.

The qualities of the heating oils and diesel fuels are laid down in more detail, for example, in DIN 51603 and EN 590 (cf. also Ullmann's Encyclopedia of Industrial Chemistry, 5th edition, volume A12, p. 617 ff.).

The inventive copolymer may, in addition to the use thereof in the middle distillate fuels of fossil, vegetable or animal origin mentioned, which are essentially hydrocarbon mixtures, also be used in mixtures of such middle distillates with biofuel oils (biodiesel) or in pure biofuel oils to improve the cold flow performance. In the context of the present invention, such mixtures and also pure biofuel oils, all of which are commercially available, are also encompassed by the term "middle distillate fuel". The mixtures mentioned may comprise the biofuel oils in minor amounts, and in that case typically in amounts of 1 to 30% by weight, especially of 3 to 10% by weight, based on the total amount of middle distillate of fossil, vegetable or animal origin and biofuel oil, or in higher amounts up to 100% by weight.

In a preferred embodiment, the inventive copolymer is used as an additive to fuels which consist of biofuel oils (A) based on fatty acid esters, or of mixtures of (A) 30 to less than 100% by weight of at least one biofuel oil based on fatty acid esters, and
(B) more than 0 to 70% by weight of middle distillates of fossil origin and/or of vegetable and/or animal origin, which are essentially hydrocarbon mixtures and are free of fatty acid esters.

Biofuel oils are generally based on alkyl esters of fatty acids which derive from vegetable and/or animal oils and/or fats. Alkyl esters are typically understood to mean lower alkyl esters, especially $C_1$- to $C_4$-alkyl esters, which are obtainable by transesterifying the glycerides, especially triglycerides, which occur in vegetable and/or animal oils and/or fats, by means of lower alcohols, for example ethanol or in particular methanol ("FAME"). Typical lower alkyl esters based on vegetable and/or animal oils and/or fats, which find use for this purpose as biofuel oil or components, are, for example, sunflower methyl ester, palm oil methyl ester ("PME"), soybean oil methyl ester ("SME") and especially rapeseed oil methyl ester ("RME").

The inventive copolymer brings about a distinct improvement in the cold flow performance of the middle distillate fuel or of the middle distillate-biofuel oil mixture, i.e. a lowering especially of the PP value, but also of the CFPP and/or the PP values, substantially irrespective of the origin or the composition of the fuel. Especially in the case of pure biofuel oils (biodiesel), this effect is clearly perceptible. The precipitated paraffin crystals are generally kept suspended more effectively, such that there is no blockage or filters and lines by such sediments. In most cases, the inventive terpolymer has a good breadth of action and thus has the effect that the precipitated paraffin crystals are dispersed very effectively in a wide variety of different fuels.

Equally, through the use of the inventive copolymer, in addition to the improvement in the cold flow properties of middle distillate fuels and in the handling with cold flow improver additives or with middle distillates comprising cold flow improver additives, for example the improvement of the filterability of the fuels, a series of further fuel properties can be improved. By way of example, merely the additional effect as an anticorrosive or the improvement in the oxidation stability shall be mentioned here.

The present invention also provides middle distillate fuels which comprise 10 to 5000 ppm by weight, especially 25 to 2000 ppm by weight, in particular 50 to 1000 ppm by weight, of the inventive copolymer.

The middle distillate fuels mentioned may comprise, as further additives in amounts customary therefor, further cold flow improvers, paraffin dispersants, conductivity improvers, anticorrosion additives, lubricity additives, antioxidants, metal deactivators, antifoams, demulsifiers, detergents, cetane number improvers, solvents or diluents, dyes or fragrances or mixtures thereof. Further cold flow improvers are described, for example, in WO 2008/113757 A1. The remaining further additives mentioned above are, incidentally, familiar to the person skilled in the art and therefore need not be explained any further.

The examples which follow are intended to illustrate the present invention, without restricting it.

EXAMPLES

Example 1

Preparation of an Inventive Copolymer 200 g (1.008 mol) of methyl undec-10-enoate were dissolved in 270 g of Solvesso® 150 and heated to 150° C. under a nitrogen atmosphere. To this were added, at 150° C. within 3 hours, 98.9 g (1.008 mol) of maleic anhydride and 3.45 g of di-tert-butyl peroxide, dissolved in 30 g of Solvesso® 150. This was followed by polymerization to completion at 150° C. for another 1 hour. The polymerization product thus obtained, which had a strictly alternating structure and a molecular weight $M_n$=1820 g/mol and $M_w$=3520 g/mol, was heated to 150° C. with 2.0 times the molar amount of 1-n-dodecanol under a nitrogen atmosphere for a duration of 6 hours. This afforded a clear, mobile liquid which was yellowish at room temperature and had an acid number of 38.1.

Use Examples 2 to 6

The copolymer prepared in Example 1 was tested in several commercial biofuel oils for its ability to lower the pour point (PP value). The table below shows the results of the pour point determinations obtained by the customary method:

| Example No. | Biofuel oil (origin) | Dosage [ppm by wt.] | PP value [° C.] |
|---|---|---|---|
| 2 | Perstorp (09/6249) RME | 0 | −12 |
|   | Perstorp (09/6249) RME | 500 | <−37 |
| 3 | Preem (09/6234) RME | 0 | −12 |
|   | Preem (09/6234) RME | 250 | <−37 |
|   | Preem (09/6234) RME | 500 | <−37 |
| 4 | RME/SME 75/25 (08/6234) | 0 | −9 |
|   | RME/SME 75/25 (08/6234) | 200 | <−37 |
| 5 | Perstorp (10/6134) RME | 0 | −12 |
|   | Perstorp (10/6134) RME | 500 | −36 |
| 6 | Polen (10/6133) RME | 0 | −12 |
|   | Polen (10/6133) RME | 500 | −39 |

The invention claimed is:

1. A copolymer, comprising:
(i) 10 to 90 mol % of repeating units of the structure W1

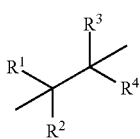

(W1)

wherein
$R^1$ and $R^2$ are each independently hydrogen, $C_1$- to $C_4$-alkyl or a carboxyl ester moiety of formula —COOR$^9$, in which $R^9$ is a $C_6$- to $C_{30}$-hydrocarbyl radical and where one of the variables $R^1$ and $R^2$ is hydrogen or $C_1$- to $C_4$-alkyl and the other is a carboxyl ester moiety of the formula —COOR$^9$, and
$R^3$ and $R^4$ are each independently hydrogen, $C_1$- to $C_4$-alkyl, a carboxyl ester moiety of the formula —COOR$^9$, in which $R^9$ is a $C_6$- to $C_{30}$-hydrocarbyl radical, or carboxyl groups which may also be present in form of alkali metal, alkaline earth metal or an ammonium salt thereof, in which one of the variables $R^3$ and $R^4$ is hydrogen or $C_1$- to $C_4$-alkyl and the other is a carboxyl ester moiety of the formula —COOR$^9$, and/or a carboxyl group which may also be present in the form of the alkali metal, alkaline earth metal or ammonium salt thereof; and
(ii) 90 to 10 mol % of repeating units of structure W2

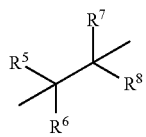

(W2)

wherein $R^5$ is a radical of a carboxylic ester of formula
-A-CO—O—R$^{10}$
in which A is a $C_1$- to $C_{20}$-alkylene group and the variable
$R^{10}$ is a $C_1$- to $C_{30}$-hydrocarbyl radical, and
$R^6$, $R^7$ and $R^8$ are each independently hydrogen or $C_1$- to $C_8$-alkyl,
wherein a sum of the repeating units W1 and W2 adds up to 100 mol %.

2. The copolymer according to claim 1, comprising from 45 to 55 mol % of repeating units of the structure W1 and from 55 to 45 mol % of repeating units of the structure W2.

3. The copolymer according to claim 1, wherein
$R^1$ is hydrogen,
$R^2$ is a carboxyl ester moiety of the formula —COOR$^9$ in which $R^9$ is a $C_8$- to $C_{16}$-hydrocarbyl radical,
$R^3$ is hydrogen,
$R^4$ is a carboxyl ester moiety of the formula —COOR$^9$ in which $R^9$ is a $C_8$- to $C_{16}$-hydrocarbyl radical, and/or a carboxyl group which may also be present in a form of the alkali metal, alkaline earth metal or ammonium salt thereof.

4. The copolymer according to claim 1, wherein
$R^5$ is a radical of a carboxylic ester of formula -A-CO—O—R$^{10}$ in which A is a linear $C_4$- to $C_{12}$-alkylene group and $R^{10}$ is a $C_1$- to $C_4$-alkyl radical, and
$R^6$, $R^7$ and $R^8$ are each hydrogen.

5. The copolymer according to claim 1, wherein the copolymer is obtained by free-radical copolymerization of
(i) 10 to 90 mol % of monomer units of structure M1

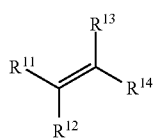

(M1)

wherein

R$^{11}$, R$^{12}$, R$^{13}$ and R$^{14}$ are each independently hydrogen, a C$_1$- to C$_4$-alkyl, a carboxyl group, a carboxyl ester moiety of formula —COOR$^{15}$ in which R$^{15}$ is a C$_1$- to C$_4$-alkyl radical, or a carbonyl halide moiety of formula —COX in which X is fluorine, chlorine, bromine or iodine, with the proviso that M1 comprises two vicinal carboxyl groups and/or carboxyl ester moieties of this kind are in cis or trans positions to one another, in which vicinal carboxyl groups in cis positions may also be present in a form of a cyclic anhydride thereof, and (ii) 90 to 10 mol % of monomer units of structure M2

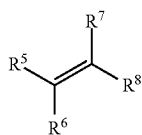

(M2)

wherein R$^5$ is a radical of a carboxylic ester of formula

-A-CO—O—R$^{10}$ wherein A is a C$_1$- to C$_{20}$-alkylene group,

R$^{10}$ is a C$_1$- to C$_{30}$-hydrocarbyl radical, and

R$^6$, R$^7$ and R$^8$ are each independently hydrogen or C$_1$- to C$_8$-alkyl, wherein a sum of the monomer units M1 and M2 adds up to 100 mol %, and subsequently polymer-analogous reaction of a product formed with at least 1 to 2 mol of a C$_6$- to C$_{30}$-hydrocarbyl alcohol per mole of monomer M1.

6. The copolymer according to claim 5, obtained by free-radical copolymerization of maleic acid, maleic anhydride, mono- or dimethyl maleate, mono- or diethyl maleate, fumaric acid, mono- or dimethyl fumarate or mono- or diethyl fumarate as monomer units M1.

7. A process for preparing a copolymer according to claim 1, comprising:

free-radically copolymerizing (i) 10 to 90 mol % of monomer units of structure M1

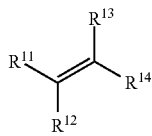

(M1)

wherein R$^{11}$, R$^{12}$, R$^{13}$ and R$^{14}$ are each independently hydrogen, C$_1$- to C$_4$-alkyl, a carboxyl group, a carboxyl ester moiety of formula —COOR$^{15}$ in which R$^{15}$ is a C$_1$- to C$_4$-alkyl radical, or a carbonyl halide moieties moiety of formula —COX in which X is fluorine, chlorine, bromine or iodine, with the proviso that M1 comprises two vicinal carboxyl groups, and/or carboxyl ester moieties of this kind are in cis or trans positions to one another, in which vicinal carboxyl groups in cis positions may also be present in a form of the cyclic anhydride thereof, and (ii) 90 to 10 mol % of monomer units of structure M2

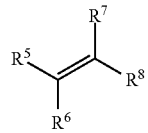

(M2)

wherein R$^5$ is the radical of a carboxylic ester of the formula

-A-CO—O—R$^{10}$ wherein A is a C$_1$- to C$_{20}$-alkylene group,

R$^{10}$ is a C$_1$- to C$_{30}$-hydrocarbyl radical, and

R$^6$, R$^7$ and R$^8$ are each independently hydrogen or C$_1$- to C$_8$-alkyl, wherein a sum of the monomer units M1 and M2 adds up to 100 mol %, with one another; and subsequently reacting the product formed in a polymer-analogous manner with at least 1 to 2 mol of a C$_6$- to C$_{30}$-hydrocarbyl alcohol per mole of monomer M1 used.

8. A middle distillate fuel comprising 10 to 5000 ppm by weight of a copolymer according to claim 1.

9. The use of a copolymer according to claim 1, wherein the copolymer is suitable for improving the cold flow properties of middle distillate fuels.

10. The copolymer according to claim 9, wherein the copolymer is an additive to fuels comprising a biofuel oil based on a fatty acid ester, or a mixture of (A) 30 to less than 100% by weight of a biofuel oil based on fatty acid esters, and (B) more than 0 to 70% by weight of middle distillates of at least one selected from the group consisting of fossil origin, vegetable origin, and animal origin, which are essentially hydrocarbon mixtures and are free of fatty acid esters.

11. The copolymer according to claim 9, wherein the copolymer is suitable for lowering a PP value of middle distillate fuels.

* * * * *

UNITED STATES PATENT AND TRADEMARK OFFICE
CERTIFICATE OF CORRECTION

| | | |
|---|---|---|
| PATENT NO. | : 8,790,424 B2 | Page 1 of 1 |
| APPLICATION NO. | : 13/432554 | |
| DATED | : July 29, 2014 | |
| INVENTOR(S) | : Ivette Garcia Castro et al. | |

It is certified that error appears in the above-identified patent and that said Letters Patent is hereby corrected as shown below:

On the title page, Item (73), the Assignee's Information is incorrect. Item (73) should read:

--(73) Assignee: BASF SE, Ludwigshafen (DE)--

Signed and Sealed this
Twenty-fifth Day of November, 2014

Michelle K. Lee
*Deputy Director of the United States Patent and Trademark Office*